US009176028B2

(12) United States Patent
ElNaggar et al.

(10) Patent No.: US 9,176,028 B2
(45) Date of Patent: Nov. 3, 2015

(54) BALL ASSISTED DEVICE FOR ANALYTICAL SURFACE SAMPLING

(71) Applicants: UT-BATTELLE, LLC, Oak Ridge, TN (US); DH Technologies Development Pte. Ltd.

(72) Inventors: Mariam S. ElNaggar, Indianapolis, IN (US); Gary J. Van Berkel, Oak Ridge, TN (US); Thomas R. Covey, Richmond Hill, CA (US)

(73) Assignees: UT-BATTELLE, LLC, Oak Ridge, TN (US); DH TECHNOLOGIES DEVELOPMENT PTE. LTD, Singapore (SG)

( * ) Notice: Subject to any disclaimer, the term of this patent is extended or adjusted under 35 U.S.C. 154(b) by 396 days.

(21) Appl. No.: 13/644,941

(22) Filed: Oct. 4, 2012

(65) Prior Publication Data

US 2014/0096624 A1 Apr. 10, 2014

(51) Int. Cl.
*G01N 1/14* (2006.01)
*G01N 1/02* (2006.01)

(52) U.S. Cl.
CPC ............ *G01N 1/14* (2013.01); *G01N 2001/028* (2013.01)

(58) Field of Classification Search
USPC .................................. 73/864–864.74, 866.5
See application file for complete search history.

(56) References Cited

U.S. PATENT DOCUMENTS

| 3,285,228 | A | 11/1966 | Fisher |
| 6,677,593 | B1 | 1/2004 | Van Berkel |
| 6,784,439 | B2 | 8/2004 | Van Berkel |
| 6,803,566 | B2 | 10/2004 | Van Berkel |
| 6,952,013 | B2 | 10/2005 | Granger |
| 7,295,026 | B2 | 11/2007 | Van Berkel et al. |
| 7,995,216 | B2 | 8/2011 | Van Berkel |
| 8,117,929 | B2 | 2/2012 | Van Berkel |
| 2003/0080143 | A1* | 5/2003 | Kale et al. .......................... 222/1 |
| 2007/0196817 | A1* | 8/2007 | Broom ............................... 435/5 |
| 2008/0124720 | A1 | 5/2008 | Sowerby et al. |
| 2010/0224013 | A1* | 9/2010 | Van Berkel et al. ....... 73/863.81 |
| 2012/0079894 | A1 | 4/2012 | Van Berkel et al. |
| 2012/0080589 | A1 | 4/2012 | Van Berkel et al. |
| 2012/0083045 | A1 | 4/2012 | Van Berkel et al. |

FOREIGN PATENT DOCUMENTS

RU 2327244 8/2006

OTHER PUBLICATIONS

Asano et al., "Self-aspirating atmospheric pressure chemical ionization source for direct sampling of analytes on surfaces and in liquid solutions", RCM (2005) 19(16): 2305-2312.

(Continued)

*Primary Examiner* — Peter Macchiarolo
*Assistant Examiner* — Alexander Mercado
(74) *Attorney, Agent, or Firm* — Novak Druce Connolly Bove + Quigg LLP

(57) ABSTRACT

A system for sampling a surface includes a sampling probe having a housing and a socket, and a rolling sampling sphere within the socket. The housing has a sampling fluid supply conduit and a sampling fluid exhaust conduit. The sampling fluid supply conduit supplies sampling fluid to the sampling sphere. The sampling fluid exhaust conduit has an inlet opening for receiving sampling fluid carried from the surface by the sampling sphere. A surface sampling probe and a method for sampling a surface are also disclosed.

25 Claims, 12 Drawing Sheets

(56) References Cited

OTHER PUBLICATIONS

Einaggar et al., "Liquid microjunction surface sampling probe fluid dynamics: Characterization and application of an analyte plug formation operational mode", Journal of the American Society Mass Spectrometry (2011) 10(22): 1737-1743.

Orsnes et al., "A rotating ball inlet for on-line MALDI mass spectrometry", Anal. Chem. (2000) 72: 251-254.

Orsnes et al., "Interfaces for on-line liquid sample delivery for matrix-assisted laser desorption ionisation mass spectrometry", Chem. Soc. Rev. (2001) 30: 104-112.

Orsnes et al., "Stopped-flow mass spectrometry with rotating ball inlet: Application to the ketone-sulfite reaction", Anal. Chem. (1998) 70(22): 4751-4754.

Van Berkel et al., "Thin-layer chromatography and electrospray mass spectrometry coupled using a surface sampling probe", Anal. Chem. (2002) 74: 6216-6223.

\* cited by examiner

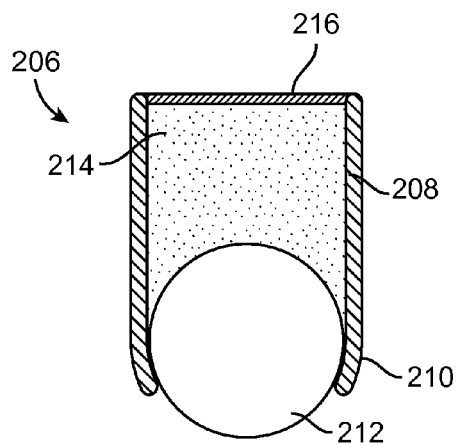
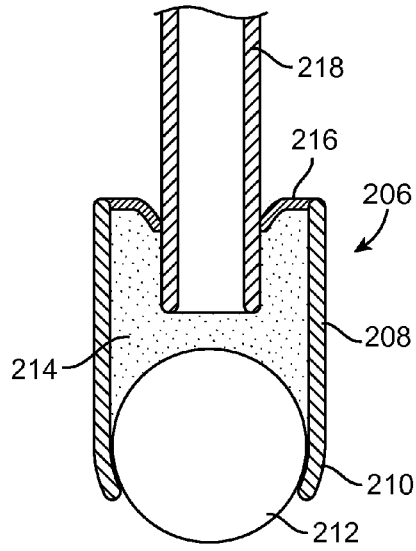
FIG. 9A  FIG. 9B
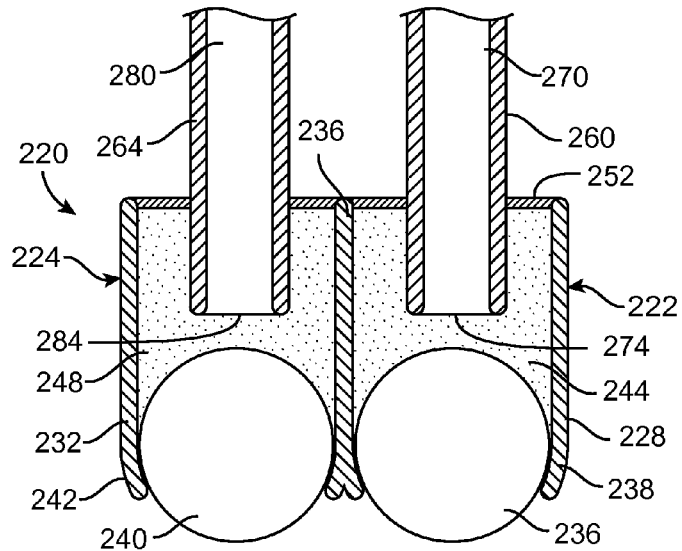
FIG. 10

BALL ASSISTED DEVICE FOR ANALYTICAL SURFACE SAMPLING

STATEMENT REGARDING FEDERALLY SPONSORED RESEARCH

This invention was made with government support under contract No. DE-AC05-00OR22725 awarded by the U.S. Department of Energy. The government has certain rights in this invention.

FIELD OF THE INVENTION

This invention relates generally to analytical surface sampling, and more particularly to analytical surface sampling incorporating a surface sampling probe.

BACKGROUND OF THE INVENTION

The automated sampling of surfaces for analytes is an area of continuing interest. Recent methodologies have utilized surface sampling probes and various forms of automation as a means of improving sampling efficiency and accuracy. Examples include those shown in U.S. Pat. No. 8,117,929, U.S. Pat. No. 7,995,216, U.S. Pat. No. 7,295,026, U.S. Pat. No. 6,952,013, U.S. Pat. No. 6,803,566, U.S. Pat. No. 6,784,439, and U.S. Pat. No. 6,677,593, US 2012/0079894, and US 2012/0080589. The disclosures of these patents and publications are hereby incorporated fully by reference.

SUMMARY OF THE INVENTION

A system for sampling a surface includes a sampling probe having a housing and a socket, and a rolling sampling sphere engaged to the probe within the socket. The housing has a sampling fluid supply conduit and a sampling fluid exhaust conduit. The sampling fluid supply conduit supplies sampling fluid to the sampling sphere. The sampling fluid exhaust conduit has an inlet opening for receiving sampling fluid carried from the surface by the sampling sphere.

An exhaust pump can be provided for withdrawing sampling fluid from the sampling fluid exhaust conduit. A supply pump can be provided for supplying sampling fluid through the sampling fluid supply conduit to the sampling sphere. The supply pump and the exhaust pump can have adjustable volumetric flow rates. The supply pump and the exhaust pump can have matched volumetric flow rates.

The system can include a sample analysis device. The sample analysis device receives sampling fluid from the sampling fluid exhaust conduit. The analysis device can be at least one selected from the group consisting of an ionization source, a separation device, and a mass spectrometer. The analysis device can be a sample collection container.

The sampling sphere can rotate in all directions about three axes. The sampling sphere can have surface structure for sample pickup. The surface structure can have at least one selected from the group consisting of surface protrusions, surface depressions, and surface coatings.

The sampling fluid supply conduit and the sampling fluid exhaust conduit can be concentric. The sampling fluid exhaust conduit can be movable to adjust the distance between the inlet opening of the sampling fluid exhaust conduit and the sampling sphere.

The rolling sphere can be completely spherical or partially spherical. A partially spherical design can be substantially in the shape of a wheel. Another partially spherical design can be a semispherical design or any part or portion of a spherical surface, or any surface that is capable of rolling movement.

The system can include a wash fluid supply conduit for supplying a wash fluid to the sampling sphere to remove sample from the sphere. The sampling fluid exhaust conduit can be concentric to the sampling fluid supply, and the wash fluid supply conduit can be concentric to and surround both the sampling fluid supply conduit and the sampling fluid exhaust conduit. The sampling fluid supply conduit and the sampling fluid exhaust conduit are retractable within the wash fluid supply conduit to permit the flow of wash fluid over the sphere.

The sampling fluid supply conduit and the sampling fluid exhaust conduit can be side by side. The system can have at least two connected probes each probe including a sampling fluid supply conduit, a rolling sphere, and a sampling fluid exhaust conduit. The sampling fluid supply conduit can be an enclosed reservoir of sampling fluid.

The system can have additional components. These components can include at least one selected from the group consisting of a camera, a battery, a global positioning system component, a processor, a wireless receiver/transmitter, an ink supply, and a motor drive.

A surface sampling probe can include a housing and a socket, and a rolling sampling sphere within the socket. The housing can have a sampling fluid supply conduit and a sampling fluid exhaust conduit. The sampling fluid supply conduit supplies sampling fluid to the sampling sphere. The sampling fluid exhaust conduit has an inlet opening for receiving sampling fluid carried from the surface by the sampling sphere.

The surface sampling probe can have additional components. These components can include at least one selected from the group consisting of a camera, a battery, a global positioning system component, a processor, a wireless receiver/transmitter, an ink supply, and a motor drive.

A method for sampling a surface includes the step of providing a surface sampling probe comprising a housing and a socket, and a rolling sampling sphere within the socket. The housing has a sampling fluid supply conduit and a sampling fluid exhaust conduit. The sampling fluid supply conduit supplies sampling fluid to the sampling sphere. The sampling fluid exhaust conduit has an inlet opening for receiving sampling fluid carried from the surface by the sampling sphere. Sampling fluid is supplied to the rolling sphere through the sampling fluid supply conduit. The sphere is rolled across a sample surface, such that the rolling sphere will carry sampling fluid to the surface, take up sample in the sampling fluid, and carry the sampling fluid toward the inlet opening of the sampling fluid exhaust conduit. Sampling fluid containing the sample is withdrawn through the sampling fluid exhaust conduit.

The method can further comprising the step of analyzing the sample with an analysis device. The analysis device can be at least one selected from the group consisting of an ionization source, a separation device and a mass spectrometer.

The rolling step and the withdrawing step can occur simultaneously. The rolling step can continue for a period of time before the withdrawing step, such that the sample can accumulate within the housing before withdrawing begins. The rolling step can include rolling the sphere about three perpendicular axes.

The distance between the inlet opening of the sampling fluid exhaust conduit and the sphere can be adjusted between the rolling step and the withdrawing step. The distance is greater during the rolling step.

The method can also include the step of washing the sphere with a washing fluid after the rolling step to remove sample from the sphere.

BRIEF DESCRIPTION OF THE DRAWINGS

There are shown in the drawings embodiments that are presently preferred it being understood that the invention is not limited to the arrangements and instrumentalities shown, wherein:

FIG. 9 A-B is a cross-section of an alternative embodiment having a sampling fluid reservoir, in first and second modes of operation.

FIG. 10 is a schematic cross-section of an alternative probe design having side by side rolling sampling spheres.

DETAILED DESCRIPTION OF THE INVENTION

The present invention relates to a system for sampling a surface. The system includes a sampling probe having a housing and a rolling sampling sphere. The rolling sampling sphere is mounted to the housing by suitable structure such as a socket. The probe housing includes a sampling fluid supply conduit and a sampling fluid exhaust conduit. The sampling fluid supply conduit supplies sampling fluid to the sampling sphere. The sampling fluid exhaust conduit includes an inlet opening for receiving sampling fluid carried from the sample surface by the sampling sphere. Many different designs for the sampling probe, the sampling sphere, the socket for mounting the sampling sphere, the sampling fluid supply conduit, and sampling fluid exhaust conduit are possible.

Figure 1:
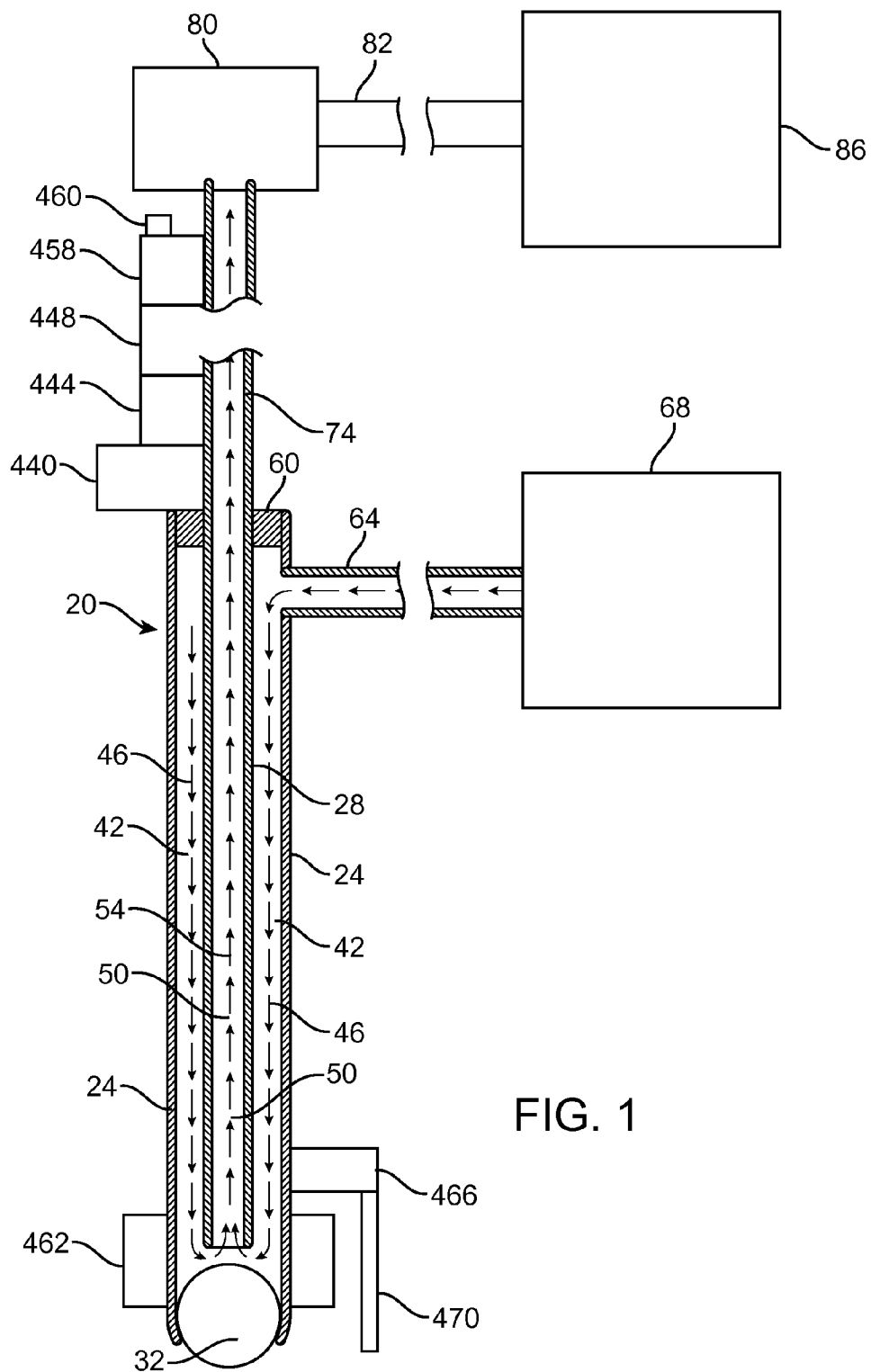
FIG. 1 is a schematic cross-section of a system for analyzing a surface.
Figure 2:
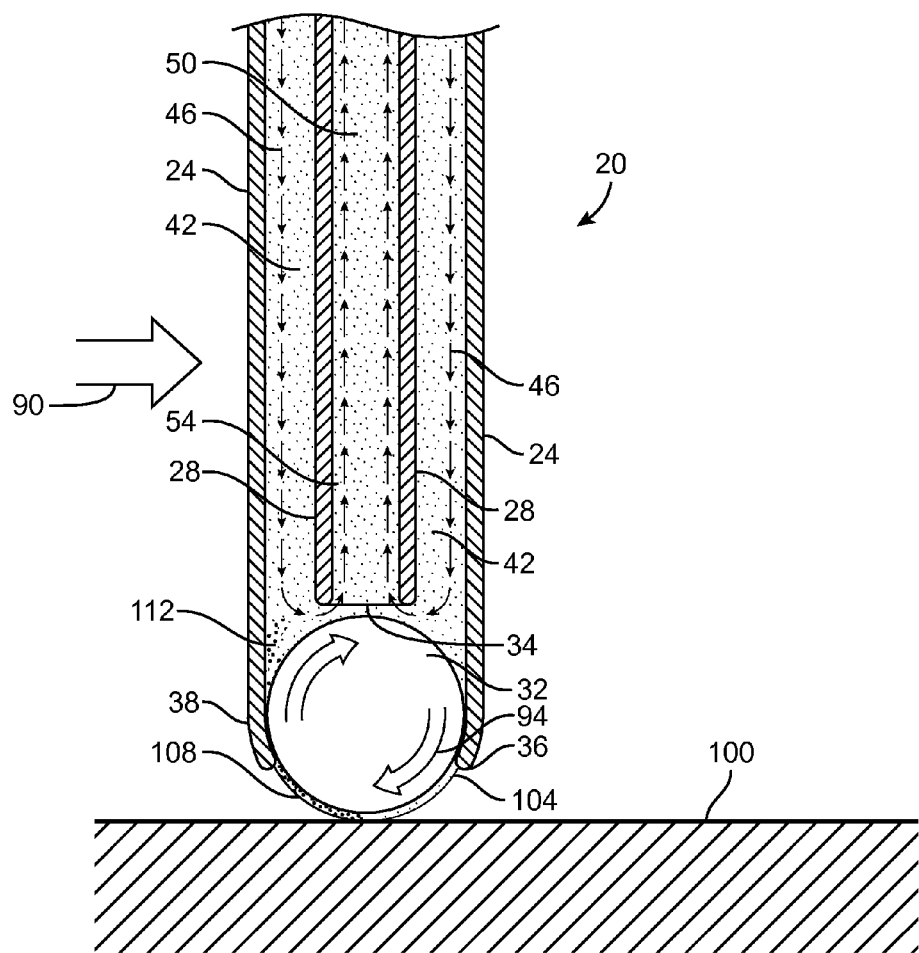
FIG. 2 is a schematic cross-section of a probe moving across a sample surface.
Figure 3:
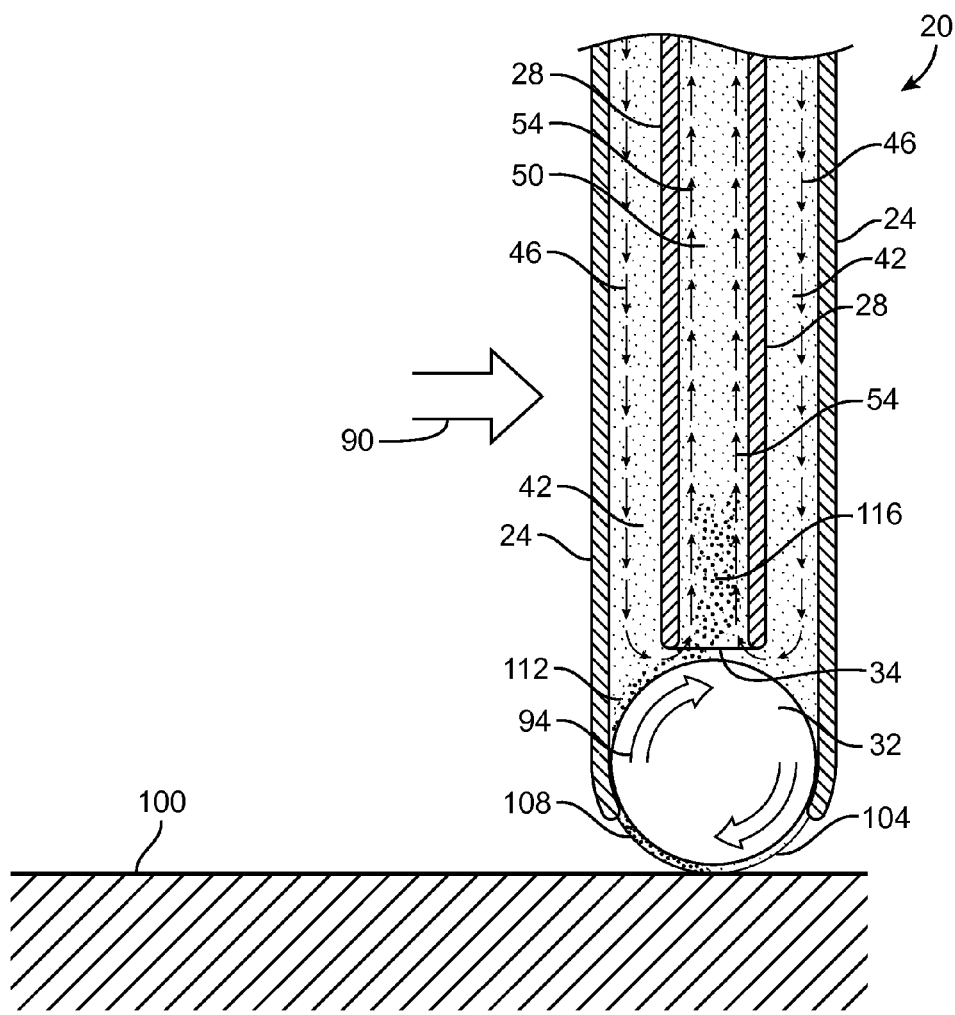
FIG. 3 is a schematic cross-section at a subsequent stage of operation.

In one embodiment shown in FIGS. 1-3, the system includes a sampling probe 20 having a housing 24 and a rolling sampling sphere 32. The rolling sampling sphere 32 is mounted to the housing by suitable structure such as socket 38. The probe housing 24 includes a sampling fluid supply conduit and a sampling fluid exhaust conduit 28. In the embodiment shown in FIGS. 1-3, the sampling fluid exhaust conduit 28 is provided within the housing 24 and the housing 24 and sampling fluid exhaust conduit 28 form there between an annular sampling fluid supply conduit 42. The sampling fluid exhaust conduit defines an inner conduit 50 having an inlet opening 34. The inlet opening 34 of the sampling fluid exhaust conduit 28 is positioned adjacent to the sphere 32 such that sample carried from the surface by the sphere 32 is drawn into the sampling fluid exhaust conduit 28. Other designs for the sampling fluid supply conduit and sampling fluid exhaust conduit are possible, for example, the sampling fluid supply conduit could be mounted within the housing 24 and the sampling fluid exhaust conduit could be formed in the annular space between the sampling fluid supply conduit and the housing.

Sampling fluid travels in the sampling fluid supply conduit 42 as shown by the arrows 46. The sampling fluid contacts the sphere 32 and is carried by the rolling sphere 32 to the surface and then back into the housing 24. The sampling fluid is withdrawn through the sampling fluid exhaust conduit 28 as indicated by the arrows 54. An end closure 60 can be provided to seal the housing 24 and sampling fluid supply conduit 42.

Sampling fluid can be supplied by a suitable sampling fluid inlet conduit 64 which communicates with a source 68 of sampling fluid. The source 68 can be a local source such as a reservoir, or a connection to a remote source of sampling fluid. The source 68 can include a pump for supplying the sampling fluid at a desired volumetric flow rate, or a controllable valve for metering the flow rate of sampling fluid into the probe 20.

Sampling fluid leaves the probe 20 through suitable structure such as an outlet portion 74 of the sampling fluid exhaust conduit 28 which can extend through the end 60. Sample fluid is routed through a suitable analysis conduit 82 to an analysis device 86. A pump 80 can be provided to withdraw the sample fluid through the sampling fluid exhaust conduit 24. Any suitable pump or mechanism, including aspiration or other fluid moving devices or methods are possible.

As shown in FIG. 2, the operation of the probe 20 begins with movement of the probe in the direction shown by arrow 90 across the surface 100 that is to be sampled. The sphere 32 rotates within the socket 38 as shown by arrows 94. Sampling fluid is carried by the rotating sphere 32 past a lower end 36 of the socket 38. The sampling fluid 104 is carried by the sphere 32 and brought into contact with the surface 100. The sampling fluid 108 that contains the sample is carried by the sphere 32 back into the housing 24 and the dissolved sample or sample particles 112 leave the sphere 32 and enter the sampling fluid within the housing 24. As shown in FIG. 3, sample particles 116 have be drawn through the inlet 34 and into the open interior 50 of the sampling fluid exhaust conduit 28 and carried by the flow of sampling fluid indicated by arrows 54 as it is withdrawn from the probe 20. The sampling of the surface 100 can be continuous with movement of the probe 20 as new sampling fluid will be carried to the surface 100 as the probe 20 is moved across the surface 100, and sampling fluid can be continuously supplied through the sampling fluid supply conduit 42 as indicated by arrows 46. Also, as the sphere 32 is capable of rotation about three perpendicular axes, the probe 20 can be moved in multiple directions across the surface 100 as samples are taken. Such movement can be manual, or movement can be controlled by a processor and by mounting the probe 20 on a robotic arm, such that movement can be precisely controlled. Alternatively, relative movement between the probe 20 and the sample surface can be effected by moving the sample relative to the probe 20.

The distance between the sphere 32 and the inlet opening 34 should be selected such that sample-containing sampling fluid is removed from the sphere 32 and enters the sampling fluid exhaust conduit 28. In some applications this distance should be no greater than 100 μm to 150 μm. The preferable distance will depend on the dimensions and geometry of the probe and the flow characteristics of the sampling fluid.

The sampling fluid can be any suitable fluid that is selected for the sample that is desired. The sampling fluid is selected to dissolve or otherwise have an affinity for or to retain the sample that is desired and carry the sample from the sample surface. The sample can be a single constituent of the sample surface 100, or a multi-constituent portion of the surface 100. The sampling fluid can for example be polar for polar samples, and nonpolar for nonpolar samples. The sampling fluid can itself have an affinity for the sample or can contain a compound with an affinity for a particular sample constituent, so as to select for this constituent from the sample surface. The sampling fluid can alternatively contain one or more constituents which bind or otherwise adhere with the sample that is desired such that the sample will be carried by the sampling fluid into the probe. The sampling fluid can be a liquid.

The type of analysis that is done by the analysis device 86 can vary. The analytical instrument or analysis device 86 can be any instrument utilized for analyzing the sampling fluid for the sample of interest. Examples of suitable analytical instruments include, but are not limited to, mass spectrometers, ionization sources, spectroscopy devices, separation methods, and combinations thereof. Exemplary ionization sources include, but are not limited to electrospray ionization, atmospheric pressure chemical ionization, electrospray chemical ionization (ESCi), atmospheric pressure photo-ionization or inductively coupled plasma. Exemplary separation methods include, but are not limited to liquid chromatography, solid phase extraction, HPLC, capillary electrophoresis, or any other liquid phase sample cleanup or separation process. Exemplary mass spectrometers ("MS") include, but are not limited to, sector MS, time-of-flight MS, quadrupole mass filter MS, three-dimensional quadrupole ion trap MS, linear quadrupole ion trap MS, Fourier transform ion cyclotron resonance MS, orbitrap MS and toroidal ion trap MS.

Figure 4:
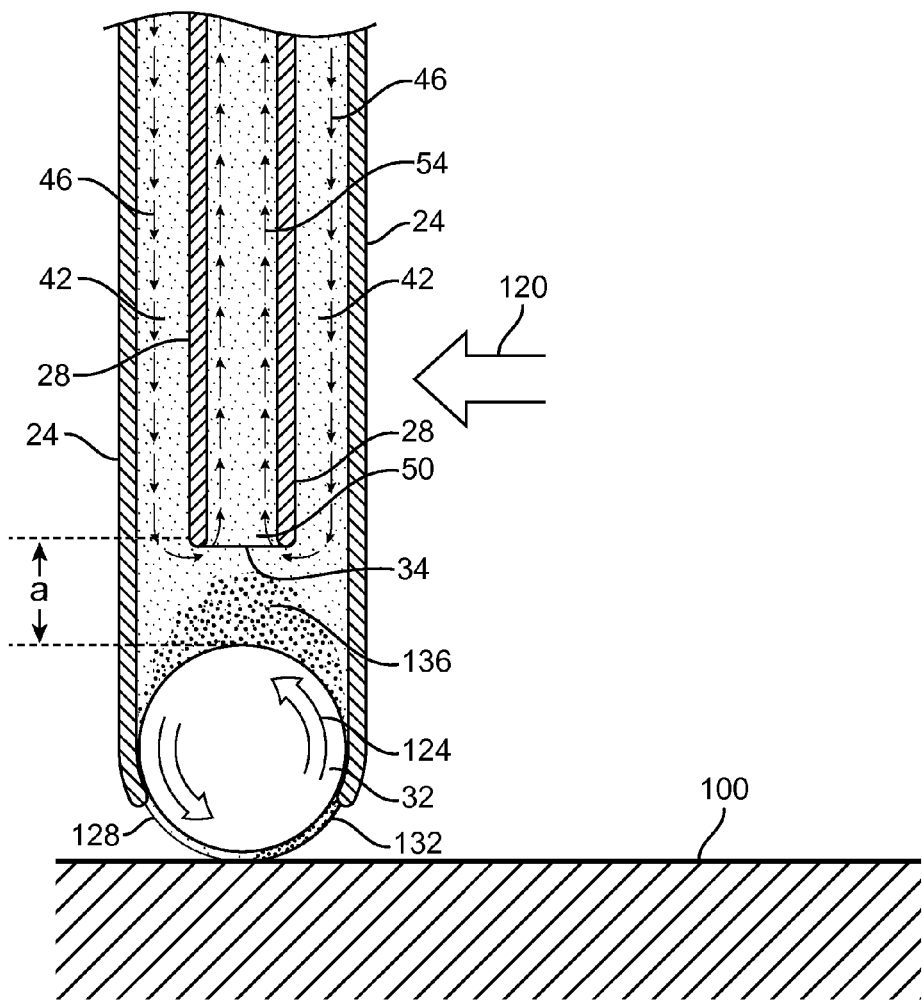
FIG. 4 is a schematic cross-section of another embodiment at a first stage of operation.
Figure 5:
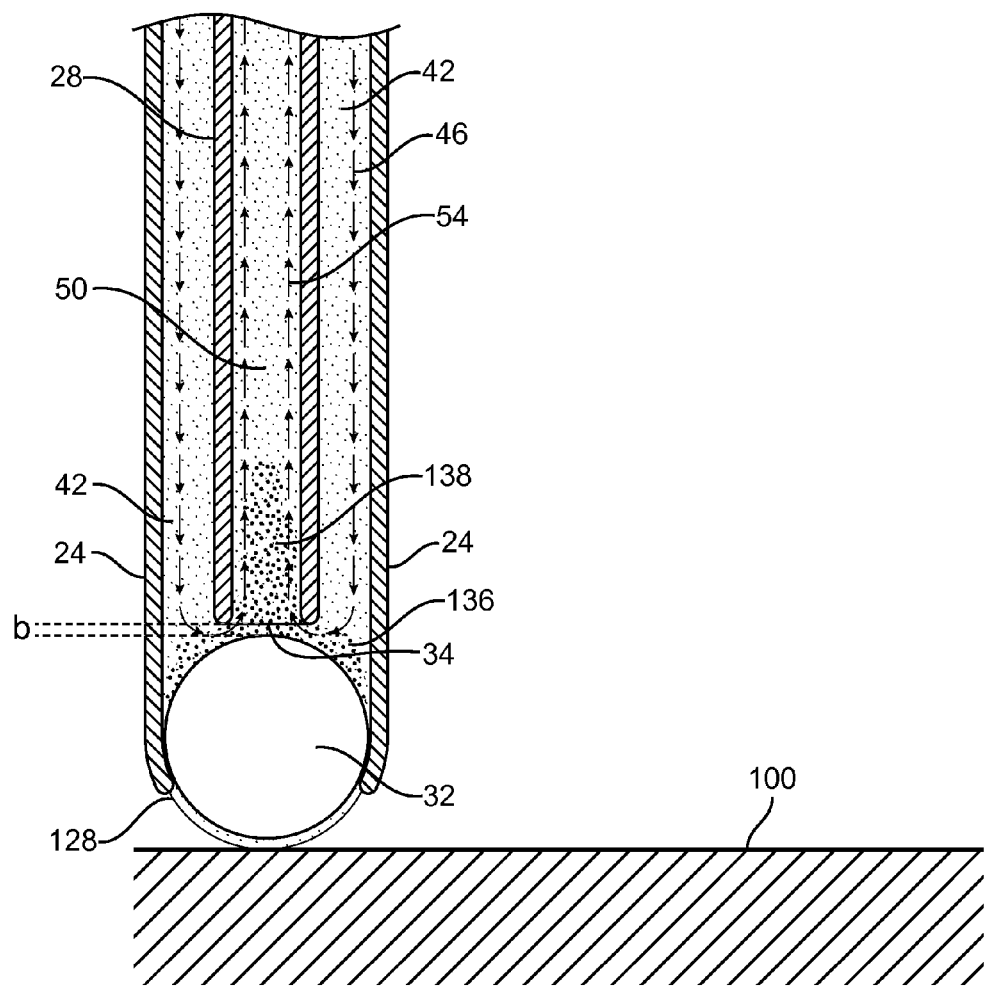
FIG. 5 is a schematic cross-section at a second stage of operation.

An alternative embodiment having a movable sampling fluid exhaust conduit 28 is shown in FIGS. 4-5. In this embodiment the sampling fluid exhaust conduit 28 is movable within the housing 24 either manually or by suitable mechanical or electromechanical devices such as a solenoid. In a first position shown in FIG. 4, the inlet opening 34 of the sampling fluid exhaust conduit 28 is positioned a distance "a" from the surface of the sphere 32 to create a space for the accumulation of sample particles. As the probe 24 is moved in the direction shown by arrow 120 the sphere 32 will rotate in the manner shown by arrows 124. Sampling fluid 128 is carried by the sphere 32 to the surface 100. Sampling fluid 132 containing sample particles is carried by the sphere 32 back into the housing 24. The sample particles 136 accumulate in the space "a". The probe 24 is moved until a sufficient supply of particles 136 have accumulated in the space "a" between the inlet opening 34 and the sphere 32. In a subsequent stage of operation shown in FIG. 5, the sampling fluid exhaust conduit 28 is moved to a position where the inlet opening 34 is closer to the surface of the sphere 32 and separated by a distance "b" that is less than the distance "a," for example less than 150 µm. As sampling fluid is withdrawn through the opening 50 as indicated by the arrows 54, sample particles 138 are drawn through the sampling fluid exhaust conduit 28 and can then be directed to a suitable analysis device.

Electrospray generally involves the flowing of a sample liquid into an electrospray ion source comprising a small tube or capillary which is maintained at a high voltage, in absolute value terms, with respect to a nearby surface. The nearby surface is commonly referred to as the counter electrode. Conventional ES systems for mass spectrometry apply high-voltage (relative to a ground reference) to the emitter electrode while holding the counter electrode at a lower, near ground reference voltage. For the positive ion mode of operation, the voltage on the emitter is high positive, while for negative ion mode the emitter voltage is high negative. The liquid introduced into the tube or capillary is dispersed and emitted as fine electrically charged droplets (plume) by the applied electrical field generated between the tube or capillary which is held at high voltage, referred to as the working electrode, and the nearby surface. The ionization mechanism generally involves the desorption at atmospheric pressure of ions from the fine electrically charged particles. The ions created by the electrospray process can then be used for a variety of applications, such as mass analyzed in a mass spectrometer.

In a typical ES-MS process, a solution containing analytes of interest is directed to the ES emitter which is held at high voltage, resulting in a charged solvent droplet spray or plume. The droplets move towards the counter electrodes under the influence of the electric field. As the droplets travel, gas-phase ions are liberated from the droplets. This process produces a quasi-continuous steady-state current with the charged droplets and ions constituting the current and completing the series circuit.

Figure 6:
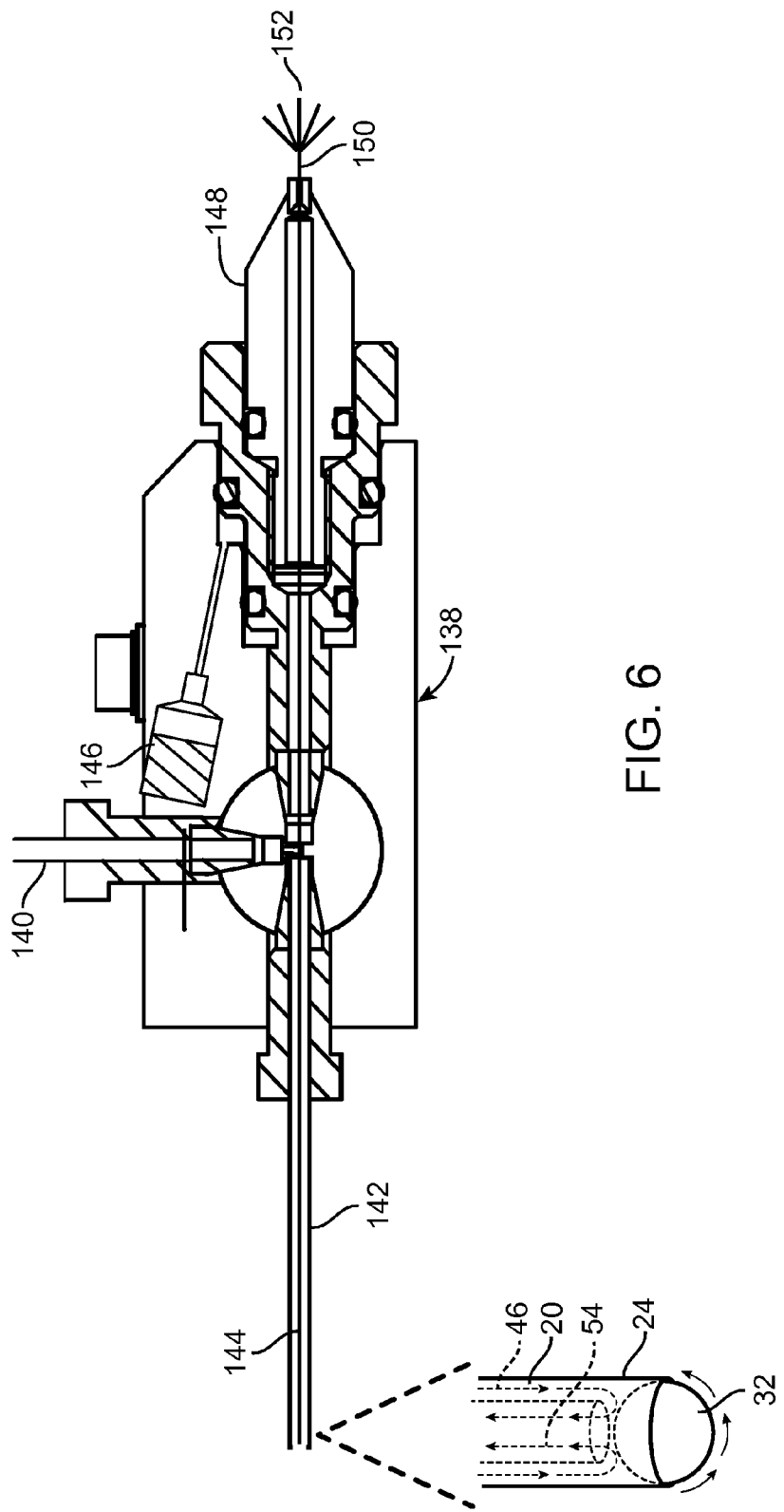
FIG. 6 is a schematic diagram of a surface analysis system according to the invention.

There is shown in FIG. 6 a microionspray device 138. The device includes a sampling fluid inlet 140 and a sampling fluid supply conduit 142. The sampling fluid exhaust conduit 144 can be provided with the sampling fluid supply conduit 142 and can be mounted within the sampling fluid supply conduit 142. The sampling fluid supply conduit 142 and sampling fluid exhaust conduit 144 can communicate with probe 20 and housing 24 to supply sampling fluid as shown by arrows 46 to rolling sphere 32. Sampling fluid including the sample is returned through a sampling fluid exhaust conduit as indicated by arrows 54. A source of nebulizing gas 146 is provided and this gas contacts the sampling fluid and sample mixture in a spray head 148. The nebulized mixture is directed through a nozzle 150 and is emitted as a spray 152. Other device constructions are possible.

Figure 7:
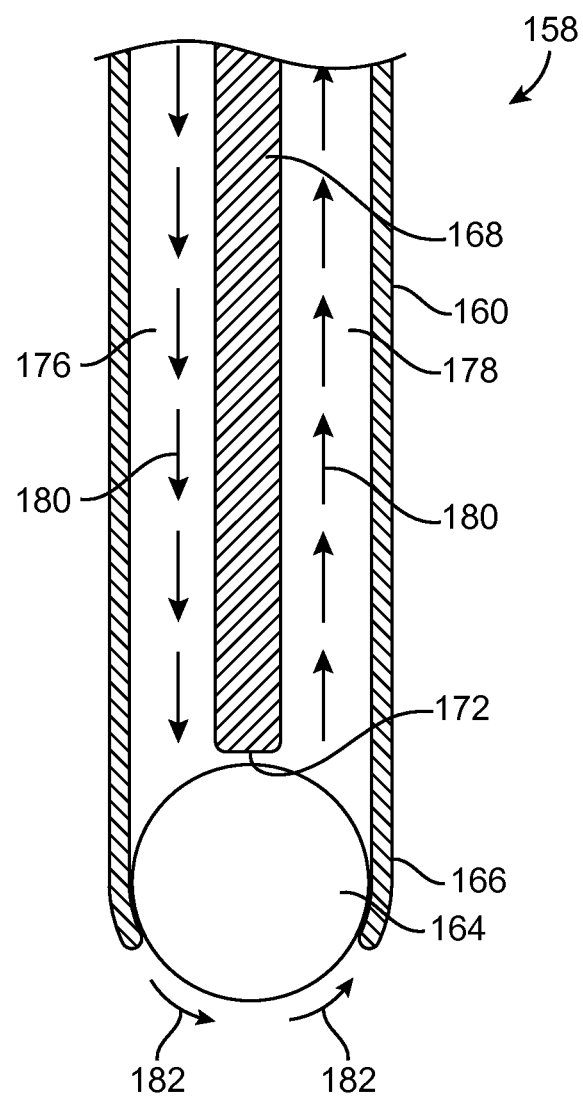
FIG. 7 is a schematic cross-section of another alternative embodiment of a probe according to the invention.

The sampling fluid supply conduit and sampling fluid exhaust conduit can be provided within the probe in a number of different configurations. There is shown in FIG. 7 a probe 158 having with a housing 160 and a rolling sphere 164 mounted within a socket 166. An inner wall 168 divides the housing 160 into a sampling fluid supply conduit 176 and a sampling fluid exhaust conduit 178. The inner wall 168 terminates at a distal end 172 that is adjacent to the rolling sphere 164. Sampling fluid flows in the direction shown by arrow 180 through the sampling fluid supply conduit 176, contacts the rolling sphere 164, and is carried by the sphere 164 to and from the sample surface as indicated by arrows 182. The sampling fluid is withdrawn from the sphere 164 and flows through the sample fluid exhaust conduit 178 in the direction shown by arrows 180.

Figure 8:
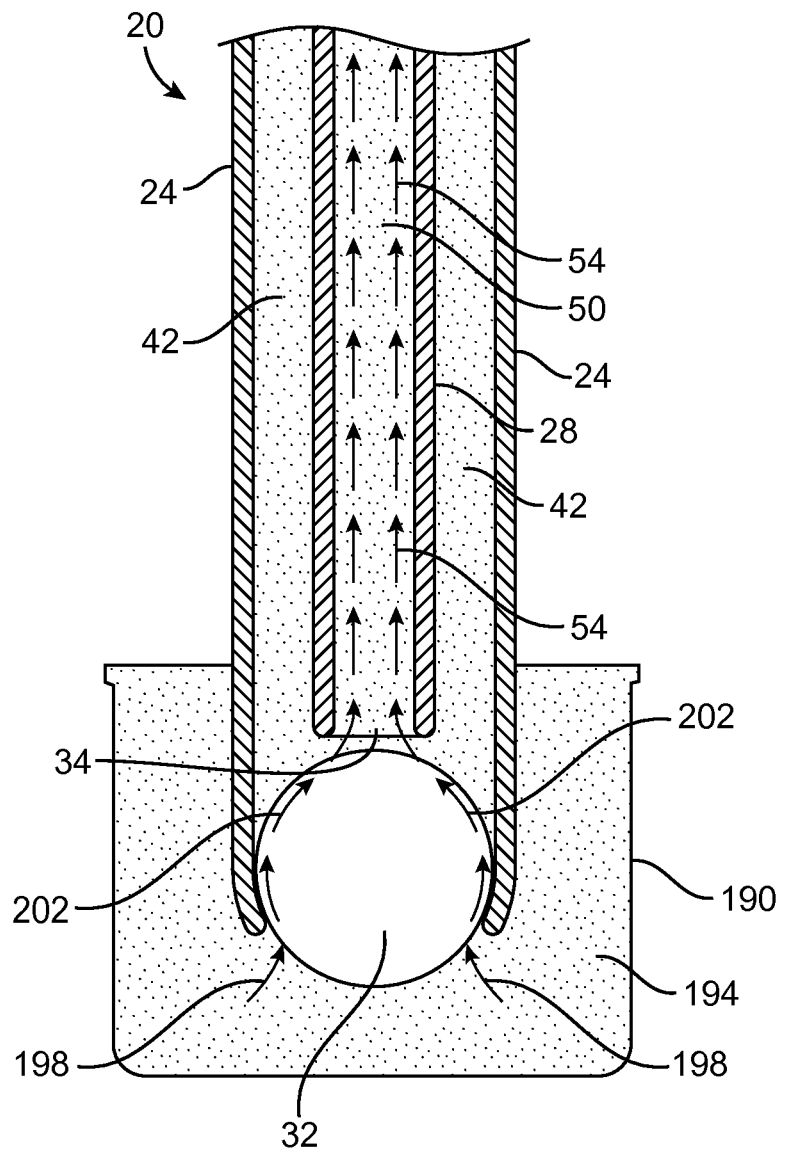
FIG. 8 is a schematic cross-section illustrating a washing step.

Some samples may adhere to the rolling sphere. In such instances it can be desirable to wash the sphere to remove sample for analysis. There is shown in FIG. 8A a probe 20 as shown in FIG. 1, where like numbers refer to like elements. In this embodiment a reservoir 190 of wash fluid 194 is provided. The probe is moved to the reservoir 190 such that the sphere 32 is at least partially immersed in the wash fluid 194. Sampling fluid is withdrawn through the inner conduit 50 as indicated by arrows 54. Wash fluid 194 from the reservoir 190 will be drawn to the sphere 32 by the suction created by the withdrawal of fluid through the sampling fluid exhaust conduit 28, as indicated by the arrows 198. The wash fluid will flow around the sphere 32 as indicated by arrows 202 and into the sampling fluid exhaust conduit 28 as indicated by arrows 54. This flow of wash fluid will wash the surface of the sphere 32 and assist in removing sample from the surface of the sphere 32. The wash fluid 194 can be the sampling fluid, or can be another fluid that is selected for the removal of sample from the sphere 32.

There is shown in FIGS. 9A-B an embodiment of a probe 206 in which a housing 208 has a socket 210 engaging a rolling sphere 212. The housing 208 encloses sampling fluid in a reservoir 214 and a seal 216 encloses the sampling fluid within the housing 208. The housing 208 and reservoir of sampling fluid 214 thereby supplies sampling fluid to the rolling sphere 212. As the sphere 212 is rolled, sampling fluid is carried by the sphere 212 to the surface and collects sample from the surface and brings the sample into the reservoir 214. Sample collected in the reservoir 214 is removed by insertion of a sampling fluid exhaust conduit 218 into the reservoir of 214. The seal 216 can be frangible such that the sampling fluid exhaust conduit 218 can be forced through the seal 216 to a position adjacent the sphere 212 such that sampling fluid and sample can be removed through the sampling fluid exhaust conduit 218. The seal 216 can alternatively be provided with a reclosable opening to permit the insertion of the sampling fluid exhaust conduit 218.

It is possible to provide multiple probes and thereby multiple rolling spheres to permit the sampling of a wider surface area in a single motion, and to permit the application of more than one sampling fluid to the sample surface in a single motion. One such device 220 is shown schematically in FIG. 10. The probe 220 includes first and second probe components 222 and 224. In the embodiment shown, the probe component 220 includes an outer housing wall 228 and an opposing outer housing wall 232 that are separated by an interior wall 236. The probe component 222 includes a rolling sphere 236 engaged by socket 238. The probe component 224 includes a rolling sphere 240 engaged by socket 242. A reservoir or supply conduit 244 of sampling fluid is provided within the probe component 222. A reservoir or supply conduit 248 of sampling fluid is provided within the probe component 224. A top seal 252 can be provided to seal the reservoirs 244 and 248. A first sampling fluid exhaust conduit 260 extends through the top seal 252 into the reservoir 244 adjacent the sphere 236. A second sampling fluid exhaust conduit 264 extends through the top seal 252 into the reservoir 248 adjacent the sphere 240. An inlet opening 274 of the sampling fluid exhaust conduit 260 is positioned adjacent the sphere 236 so as to remove sample through interior channel 270. An inlet opening 284 of the sampling fluid exhaust conduit 264 is positioned adjacent the sphere 240 so as to remove sample through the interior channel 280. Alternative constructions are possible, including probes with concentric sampling fluid supply conduits and sampling fluid exhaust conduits. Different sampling fluids can be supplied to the probe components 222 and 224. Alternatively the same sampling fluid can be provided and multiple rolling spheres can be used to sample greater surface area in a single pass. The embodiment is scalable such that any number of connected probes is possible. Also, multiple spheres could be mounted to a manifold which communicates to a single sampling fluid supply conduit, a single sampling fluid exhaust conduit, or both.

Figure 11:
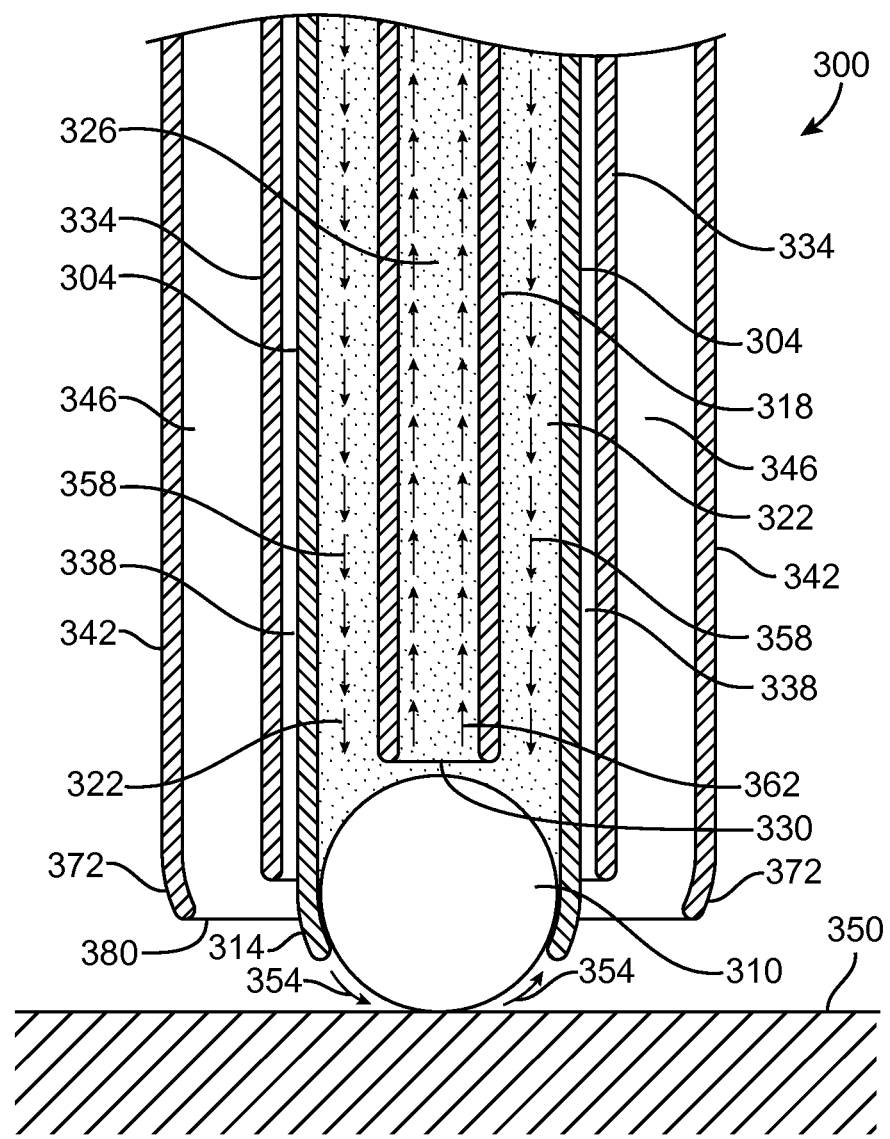
FIG. 11 is a schematic cross-section of an alternative embodiment in a first stage of operation.
Figure 12:
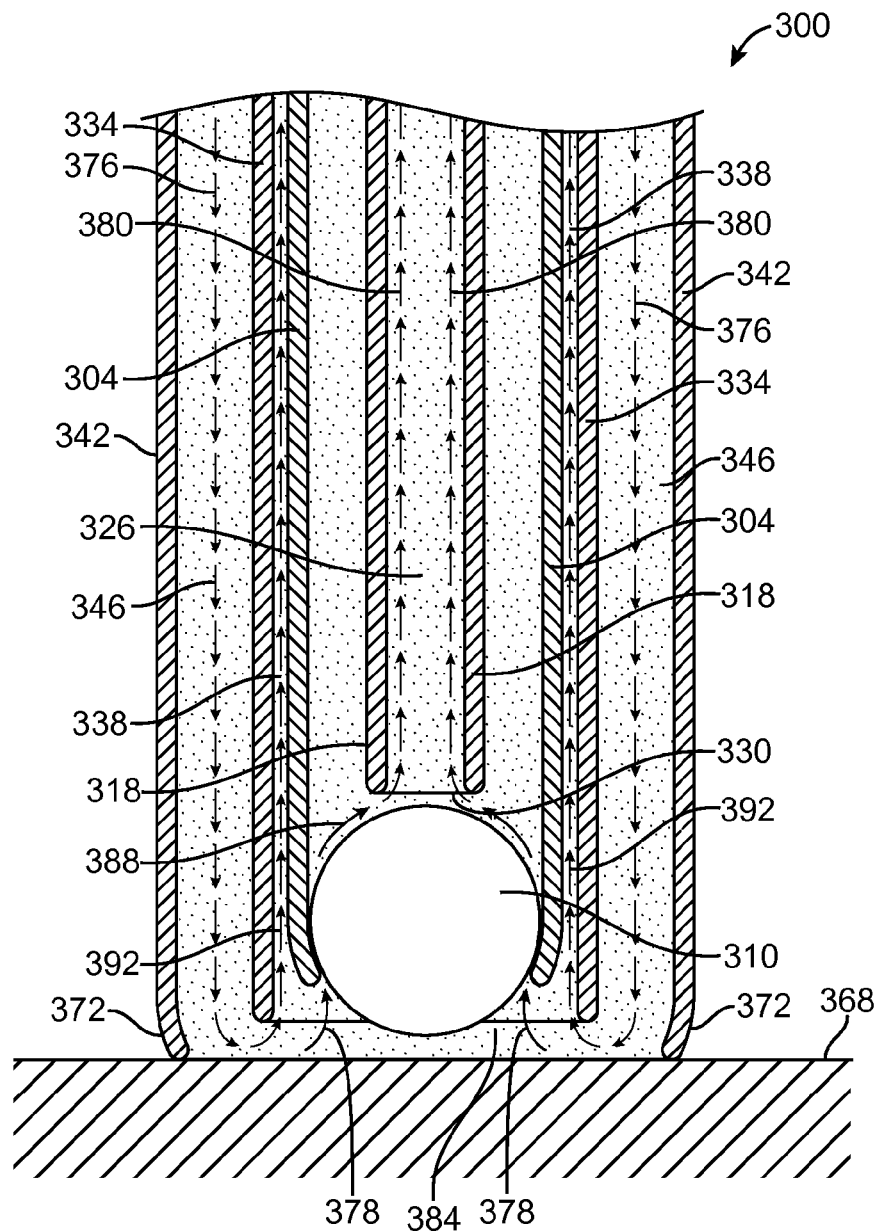
FIG. 12 is a schematic cross-section in a second stage of operation.

An alternative embodiment providing for washing of the rolling sphere is shown in FIGS. 11-12. In this embodiment, the probe 300 includes a housing 304 and a concentrically mounted sampling fluid exhaust conduit 318 having an inlet opening 330. The exhaust conduit 318 and housing 304 together define a sampling fluid supply conduit 322. The rolling sphere 310 is mounted in a suitable socket 314. An inner wash housing wall 334 is concentrically mounted about the housing 304. An outer wash housing wall 342 is concentrically mounted about the inner wash housing wall 334. A wash fluid exhaust conduit 338 is provided between the housing 304 and inner wash housing wall 334. A wash fluid supply conduit 346 is provided between the inner wash housing wall 334 and outer wash housing wall 342.

In a first mode of operation shown in FIG. 11, sampling fluid is supplied through the sampling fluid supply conduit 322 in the direction shown by arrows 358. The sampling fluid contacts the rolling sphere 310 and is carried by the sphere 310 in the direction shown by the arrows 354 and into contact with the surface 350 that is to be sampled. Sampling fluid containing the sample is returned to the housing 304 and withdrawn through the sampling fluid exhaust channel 326 of the sampling fluid exhaust conduit 318 as indicated by arrows 362. The outer wash housing wall 342 is maintained in a retracted position such that the lower edge 380 of the lower end 372 is maintained at an elevated position above the surface 350 so that sphere 310 can freely roll across the surface 350 as shown.

Sample that has accumulated on the sphere 310 can be removed by the process shown in FIG. 12. The outer wash housing wall 342 is lowered relative to the housing 304 and a rolling sphere 310, or the housing 304 and sphere 310 are retracted within the outer wash housing wall 342 such that the lower edge 380 of the lower end 372 of the outer wash housing wall 342 can form a seal with a surface. The surface can be the surface 350 that is a sample surface, or another surface 368 that is provided for the washing function, for example a sterile surface that will not contaminate the sample. A seal is thereby provided to prevent the escape of wash fluid during the wash cycle. In some instances a seal with a surface may not be necessary to prevent the escape of wash fluid, as aspiration of the wash fluid could be sufficient to prevent the escape of wash fluid, particularly if the walls and conduits are adjustable when the sphere is not rolling. Alternatively, a sealing structure or gate of some kind can be provided with the probe 300 to close the opening formed by lower edge 380 of the outer wash housing wall 342 during the wash cycle.

Figure 13:
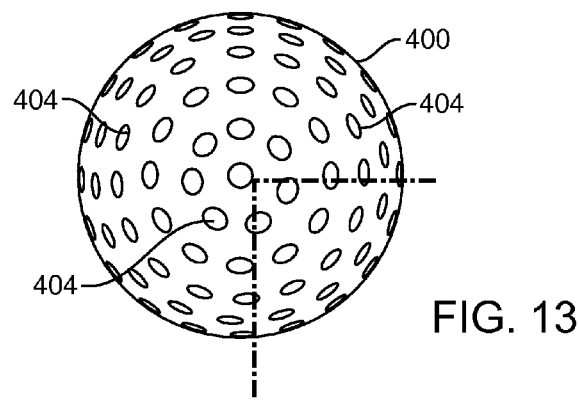
FIG. 13 is a front elevation of an alternative rolling sphere having A) surface depressions; B) surface coatings; and C) surface protrusions.
Figure 13A:
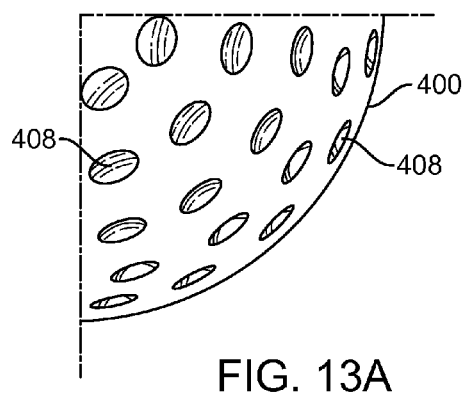
Figure 13B:
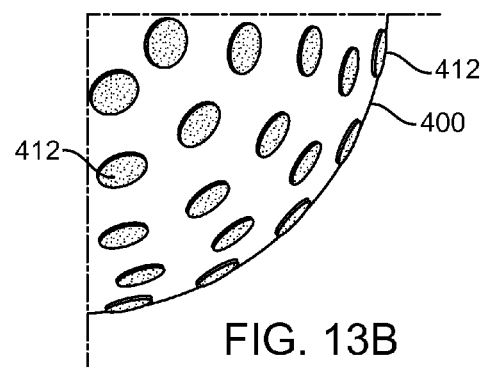
Figure 13C:
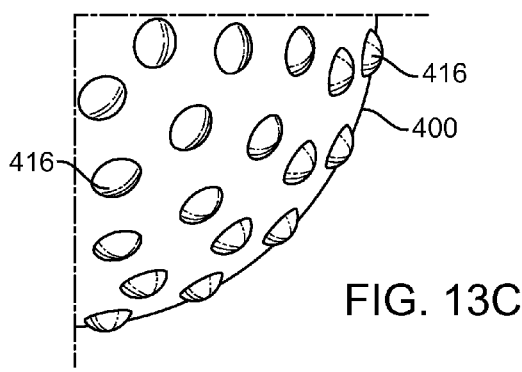

The rolling sphere can be constructed to facilitate the sampling of the surface. There is shown in FIG. 13 a sphere 400 which has a number of surface modifications 404 which are particularly suited to facilitate the sampling of the surface. The surface modifications 404 can be any suitable modifications which enhance or encourage the removal of the sample from the surface or the dissolution or adherence of the sample material to the sphere 400. The surface modifications can be continuous over substantially the entire surface of the sphere 400 or discontinuous portions such as the modifications 404. In one aspect, the modifications can be depressions 408 as shown in FIG. 13A. The depressions 408 can have differing widths and depths. Also the depressions 408 can be filled or coated with a material which has an affinity for the material that is being sampled. There are shown in FIG. 13B a sphere 400 which has been provided with surface coatings 412 of an affinity material. The affinity material can the material which binds, bonds or adheres to the sampled material to facilitate the removal of the sample by the sphere 400. Also, the surface modifications can include projections or protrusions 416 as shown in FIG. 13C. The projections 416 can have varying heights and widths. The projections 416 can serve to mechanically disrupt the surface as the sphere 400 is rolled across it so as to dislodge sample and facilitate the dissolution of the sample in the sampling fluid that is carried by the sphere 400. The projections 416 can also the coated with a material having some affinity for the sample.

The lower edge 384 of the inner wash housing wall 334 is positioned at a distance from the surface 368 and also from the lower edge 380 of the outer wash housing wall 342. Wash fluid can then flow through the wash fluid supply conduit 346 in the direction shown by arrows 376 and will flow under lower edge 384 of the inner wash housing wall 334 as shown by arrows 378 and contact the sphere 310. The wash fluid will flow over the sphere 310 as shown by arrows 388 and through the sampling fluid exhaust channel 326 of the sampling fluid exhaust conduit 318 as shown by arrows 380. Wash fluid can also flow through the wash fluid exhaust conduit 338 as shown by the arrows 392. The outer wash housing wall 342 can be repositioned relative to the housing 304 when the wash cycle has been completed. Movement of the components can be automated with solenoids or other suitable drive mechanisms, and controlled by programmable logic controllers and processors.

The sampling fluid may be supplied to the sampling fluid supply conduit by a suitable pump mechanism and may be withdrawn through the sampling fluid exhaust conduit by a suitable pump mechanism. The pump can be a syringe pump or a more automated mechanical pump. The rate of withdrawal of the sampling fluid should be balanced with the rate at which sampling fluid is supplied to the probe. The flow rate of sampling fluid into the probe can be metered and the flow rate of sampling fluid leaving the probe can be metered by suitable sensors and this information can be supplied to a suitable processor for control of the pumps. The supply pump and the exhaust pump can have adjustable volumetric flow rates, and these flow rates can be matched and slaved to one another to provide balanced flow into and out of the probe.

The rolling sphere can be completely spherical or partially spherical. A partially spherical design can be substantially in the shape of a wheel. Another partially spherical design can be a semispherical design or any part or portion of a spherical surface, or any surface that is capable of rolling movement.

The socket into which the rolling sphere is mounted can vary. The socket can have a concave surface to substantially mate with the convex surface of the sphere. The socket can retain the sphere by any suitable mechanism. It is possible to mount the sphere by providing a socket which will spring fit about the sphere past the midpoint of the sphere such that the diameter of the opening of the socket is less than the diameter of the sphere. This will permit a portion of the sphere to extend out of the socket so as to contact the sample surface. Other mechanisms for mounting the sphere in a socket and socket designs are possible. It is alternatively possible to mechanically mount the sphere in the socket about an axle, however, this will limit the range of rotation of the sphere in the socket. The socket engages the sphere in a manner which permits a surface coating of sampling fluid to escape from the probe on the rolling sphere so as to contact the sample surface. The distance between the sphere surface and the socket can be adjusted to permit the adequate escape of sampling fluid on the sphere and the return of the sampling fluid to the probe housing on the sphere.

The supply conduit and exhaust conduit designs can vary. In one aspect the conduits are tubular, but other geometries are possible. Either or both of the supply conduit and the exhaust conduit can be in the form of a reservoir. The supply conduit and exhaust conduit can be concentrically mounted, mounted side-by-side, or positioned otherwise to deliver sampling fluid to the sampling sphere and to remove sampling fluid with the sample therein from the sphere for analysis.

It is also possible to provide a stand-alone probe with one or more additional components. There is shown in FIG. 1 modifications to the probe 20 that can include a battery 444 to supply power to the probe 20 without the need of an external power source. A processor 448 can be supplied to control operation of the device, and to record results and other details of the sampling procedure. A camera 440 such as a charge coupled device (CCD) camera for recording the sampling procedure. A global positioning system (GPS) component 458 can be provided to record positional information of the probe during the sampling procedure. Data storage can be provided with the probe to record the sampling procedure. A wireless receiver/transmitter 460 can be provided to permit communication with remote data collection or probe control devices or processors. The sampling fluid source 68 and analysis device 86 can be provided in an integral, portable construction with the probe 20 or by including these components in a housing. A motor drive 462 shown schematically can be provided to when in operation engage the surface a drive the probe 20 across the surface. An ink supply source 468 can be provided with a suitable applicator 470 to supply a tracking ink to the sample surface to highlight and identify the sampling tracks with the camera 440.

This invention can be embodied in other forms without departing from the spirit or essential attributes thereof and accordingly reference should be had to the following claims as indicating the scope of the claims.

We claim:

1. A system for sampling a surface, comprising a sampling probe comprising a housing and a socket, and a rolling sampling sphere engaged in the socket, the housing having a sampling fluid supply conduit and a sampling fluid exhaust conduit, the sampling fluid supply conduit supplying sampling fluid to the sampling sphere, the sampling fluid exhaust conduit having an inlet opening for receiving sampling fluid carried from the surface by the sampling sphere, the inlet opening being spaced from the sampling sphere, the space providing a direct fluid flow path between the supply conduit, the sampling sphere, and the inlet opening, and further comprising at least one pump for continuously moving sampling fluid through the sampling fluid supply conduit to the sampling sphere and through the sampling fluid exhaust conduit, a portion of the fluid moving out of the housing with the sampling sphere to contact the surface and a portion of the fluid flowing through the direct fluid flow path, whereby fluid flowing through the direct fluid flow path will remove sample from the rolling sampling sphere and carry the sample to the exhaust conduit inlet opening.

2. The system of claim 1, wherein the at least one pump comprises a supply pump and an exhaust pump, and wherein the supply pump and the exhaust pump have adjustable volumetric flow rates.

3. The system of claim 2, wherein the supply pump and the exhaust pump have matched volumetric flow rates.

4. The system of claim 1, further comprising an analysis device, the analysis device receiving sampling fluid from the sampling fluid exhaust conduit.

5. The system of claim 3, wherein the analysis device is at least one selected from the group consisting of a mass spectrometer, an ionization source, and a separation device.

6. The system of claim 1, wherein the sampling sphere rotates in all directions about three perpendicular axes.

7. The system of claim 1, wherein the sampling sphere comprises surface structure for sample pickup.

8. The system of claim 1, wherein the surface structure comprises at least one selected from the group consisting of surface protrusions, surface depressions, and surface coatings.

9. The system of claim 1, wherein the sampling fluid exhaust conduit is movable to adjust the distance between the inlet opening of the sampling fluid exhaust conduit and the sampling sphere.

10. The system of claim 1, wherein the sampling fluid supply conduit and the sampling fluid exhaust conduit are concentric.

11. A system for sampling a surface, comprising a sampling probe comprising a housing and a socket, and a rolling sampling sphere engaged in the socket, the housing having a sampling fluid supply conduit and a sampling fluid exhaust conduit, the sampling fluid supply conduit supplying sampling fluid to the sampling sphere, the sampling fluid exhaust conduit having an inlet opening for receiving sampling fluid carried from the surface by the sampling sphere, and further comprising a supply pump for supplying sampling fluid through the sampling fluid supply conduit to the sampling sphere, and an exhaust pump for withdrawing sampling fluid from the sampling fluid exhaust conduit;

further comprising a wash fluid supply conduit for supplying a wash fluid to the sampling sphere to remove sample from the sphere, wherein the sampling fluid exhaust conduit is concentric to and within the sampling fluid supply, and the wash fluid supply conduit is concentric to and surrounds both the sampling fluid supply conduit and the sampling fluid exhaust conduit, and wherein the sampling fluid supply conduit and the sampling fluid exhaust conduit are retractable within the wash fluid supply conduit to permit the flow of wash fluid over the sphere.

12. The system of claim 1, wherein the sampling fluid supply conduit and the sampling fluid exhaust conduit are side by side.

13. The system of claim 1, comprising at least one additional probe, the probes being connected, each probe comprising a sampling fluid supply conduit, a rolling sphere, and a sampling fluid exhaust conduit.

14. The system of claim 1, wherein the sampling fluid supply conduit is an enclosed reservoir of sampling fluid.

15. The system of claim 1, further comprising at least one selected from the group consisting of a camera, a battery, a global positioning system component, a processor, a wireless receiver/transmitter, an ink supply, and a motor drive.

16. A surface sampling probe comprising a housing and a socket, and a rolling sampling sphere within the socket, the housing having a sampling fluid supply conduit and a sampling fluid exhaust conduit, the sampling fluid supply conduit supplying sampling fluid to the sampling sphere, the sampling fluid exhaust conduit having an inlet opening for receiving sampling fluid carried from the surface by the sampling sphere, the inlet opening being spaced from the rolling sampling sphere, the space providing a direct fluid flow path between the supply conduit, the sampling sphere, and the inlet opening, wherein sampling fluid moves continuously through the sampling fluid supply conduit to the sampling sphere and through the sampling fluid exhaust conduit, a portion of the fluid moving out of the housing with the sampling sphere to contact the surface and then returning with the sampling sphere into the housing, and a portion of the fluid flowing through the direct fluid flow path, whereby fluid flowing through the direct fluid flow path will remove solvent and sample from the rolling sampling sphere and carry the sample to the exhaust conduit inlet opening.

17. The surface sampling probe of claim 16, further comprising at least one selected from the group consisting of a camera, a battery, a global positioning system component, a processor, a wireless receiver/transmitter, an ink supply, and a motor drive.

18. A method for sampling a surface, comprising the steps of: providing a surface sampling probe comprising a housing and a socket, and a rolling sampling sphere within the socket, the housing having a sampling fluid supply conduit and a sampling fluid exhaust conduit, the sampling fluid supply conduit supplying sampling fluid to the sampling sphere, the sampling fluid exhaust conduit having an inlet opening for receiving sampling fluid carried from the surface by the sampling sphere; supplying with a sampling fluid to the rolling sphere through the sampling fluid supply conduit, the inlet opening being spaced from the sampling sphere, the space providing a direct fluid flow path between the supply conduit, the rolling sampling sphere, and the inlet opening, wherein sampling fluid moves continuously through the sampling fluid supply conduit to the sampling sphere and through the sampling fluid exhaust conduit, a portion of the fluid moving out of the housing with the rolling sampling sphere to contact the surface and returning with the rolling sampling sphere into the housing, and a portion of the fluid flowing through the direct fluid flow path; 5 of 11 rolling the sphere across a sample surface, whereby the rolling sphere will carry sampling fluid to the surface, take up sample in the sampling fluid, and carry the sampling fluid toward the inlet opening of the sampling fluid exhaust conduit, and whereby fluid flowing through the direct fluid flow path will remove sample from the rolling sampling sphere and carry the sample to the exhaust conduit inlet opening; and, withdrawing sampling fluid containing the sample through the sampling fluid exhaust conduit.

19. The method of claim 18, further comprising the step of analyzing the sample with an analysis device.

20. The method of claim 18, wherein the analysis device is at least one selected from the group consisting of a mass spectrometer, an ionization source, and a separation device.

21. The method of claim 18, wherein the rolling step and the withdrawing step occur simultaneously.

22. The method of claim 18, wherein the rolling step continues for a period of time before the withdrawing step, whereby sample can accumulate within the housing before withdrawing begins.

23. The method of claim 18, wherein the rolling step comprises rolling the sphere about three axes.

24. The method of claim 18, wherein the distance between the inlet opening of the sampling fluid exhaust conduit and the sphere is adjusted between the rolling step and the withdrawing step, the distance being greater during the rolling step.

25. The method of claim 18, further comprising the step of washing the sphere with a washing fluid after the rolling step to remove sample from the sphere.

* * * * *